United States Patent [19]

Asayama et al.

[11] Patent Number: 4,586,476

[45] Date of Patent: May 6, 1986

[54] AIR-TO-FUEL RATIO DETECTOR FOR ENGINES

[75] Inventors: Yoshiaki Asayama; Seiya Kominami, both of Hyogo, Japan

[73] Assignee: Mitsubishi Denki Kabushiki Kaisha, Tokyo, Japan

[21] Appl. No.: 660,274

[22] Filed: Oct. 12, 1984

[30] Foreign Application Priority Data

Oct. 14, 1983 [JP] Japan .................................. 58-192889
Nov. 24, 1983 [JP] Japan .................................. 58-221087

[51] Int. Cl.⁴ .............................................. F02B 33/00
[52] U.S. Cl. ................................... 123/440; 204/406; 204/407; 204/421; 204/426
[58] Field of Search ................ 123/489, 440; 204/425, 204/406, 407, 421

[56] References Cited

U.S. PATENT DOCUMENTS

| | | | |
|---|---|---|---|
| 4,224,113 | 9/1980 | Kimura | 204/1 T |
| 4,226,692 | 10/1980 | Isenberg | 204/19 SS |
| 4,272,329 | 6/1981 | Hetrick et al. | 123/440 |
| 4,334,510 | 6/1982 | Croset | 123/440 |

FOREIGN PATENT DOCUMENTS 54-158992 12/1979 Japan .................................. 123/440

OTHER PUBLICATIONS

Oxygen Sensing by Electrochemical Pumping–Hetrick et al., Appl. Phys. Lett. 38(5), Mar. 1, 1981.

Primary Examiner—Ronald B. Cox
Attorney, Agent, or Firm—Bernard, Rothwell & Brown

[57] ABSTRACT

An air-to-fuel ratio detector for detecting the air-to-fuel ratio of the combustible mixture supplied to an engine on the basis of the concentration of oxygen gas in the exhaust gas of the engine, comprising an air-to-fuel ratio sensor provided to detect the oxygen gas concentration in the exhaust gas and consisting of an oxygen pump and an oxygen sensor which are disposed with a minute gap therebetween, and changeover means for simultaneously changing the direction of the pump current supplied to the oxygen pump and the polarity of the detection output signal given by the oxygen sensor; thereby capable of obtaining an air-to-fuel ratio detection signal when the operating air-to-fuel ratio is either in the rich air-to-fuel region or in the lean air-to-fuel region with respect to the stoichiometric air-to-fuel ratio.

6 Claims, 5 Drawing Figures

AIR-TO-FUEL RATIO DETECTOR FOR ENGINES

BACKGROUND OF THE INVENTION

1. Field of the Invention

The present invention relates to an air-to-fuel ratio detector (designated as "A/F ratio detector" hereinafter) for detecting the air-to-fuel ratio (designated as "A/F ratio" hereinafter) of the combustible air/fuel mixture supplied to an internal-combustion engine for an automobile or the like and more particularly to an oxygen pump type A/F ratio detector employing an ion-conductive solid electrolyte.

2. Description of the Prior Art

It is generally known to control the combustible mixture so that an engine, for example, an automotive engine, can provide a combustible mixture of a stoichiometric A/F ratio by detecting the condition of combustion at the stoichiometric A/F ratio on the basis of the change of the electromotive force resulting from the difference between the oxygen partial pressure and the air partial pressure in the exhaust gas measured by an oxygen sensor having an ion-conductive solid electrolyte such as stabilized zirconia. However, such an oxygen sensor has a disadvantage that the output of the oxygen sensor varies greatly when the A/F ratio of the combustible mixture is around the stoichiometric A/F ratio, whereas the output of the oxygen sensor varies only slightly when the operating A/F ratio is an A/F ratio other than the stoichiometric A/F ratio, and hence the output of the oxygen sensor can not be used for controlling the operation of the engine when the engine is operated at an A/F ratio other than the stoichiometric A/F ratio.

SUMMARY OF THE INVENTION

Accordingly, it is an object of the present invention to provide a novel A/F ratio detector capable of detecting the operating A/F ratio accurately over a wide range of A/F ratio.

The principle of the present invention is based on a fact that, in an A/F ratio sensor consisting of an oxygen pump and an oxygen sensor, the A/F ratio detecting range is shifted from a range over the stoichiometric A/F ratio to a range below the stoichiometric A/F ratio and vice versa when the direction of the electric current supplied to the oxygen pump is changed.

An A/F ratio detector according to the present invention comprises: an A/F ratio sensor having an oxygen pump and an oxygen sensor disposed opposite to each other with a minute gap therebetween in the exhaust gas passage of an engine and each being formed by attaching electrodes to the opposite sides of a flat plate of a solid electrolyte respectively; current supply means to supply a pump current to the oxygen pump; electromotive force detecting means to detect the magnitude of an electromotive force generated proportionally to the difference between the oxygen partial pressure within the gap and the oxygen partial pressure outside the gap by the oxygen sensor supplied with a predetermined pump current; pump current control means to control the pump current to be supplied to the oxygen pump so that the electromotive force detected by the electromotive force detecting means is maintained at a fixed level; means to give an A/F ratio detection output which is proportional to the pump current; and changeover means to change over the direction of the pump current supplied to the oxygen pump and the polarity of the output signal of the oxygen sensor simultaneously.

The present invention provides also an A/F ratio control unit capable of controlling the A/F ratio accurately over a wide range of A/F ratio through the feedback control of the A/F ratio of the combustible mixture supplied to the engine, on the basis of the A/F ratio detection output by actuating the changeover means when the operating A/F ratio is changed from a lean region to a rich region with respect to the stoichiometric A/F ratio.

DETAILED DESCRIPTION OF THE PREFERRED EMBODIMENT

Figure 1:
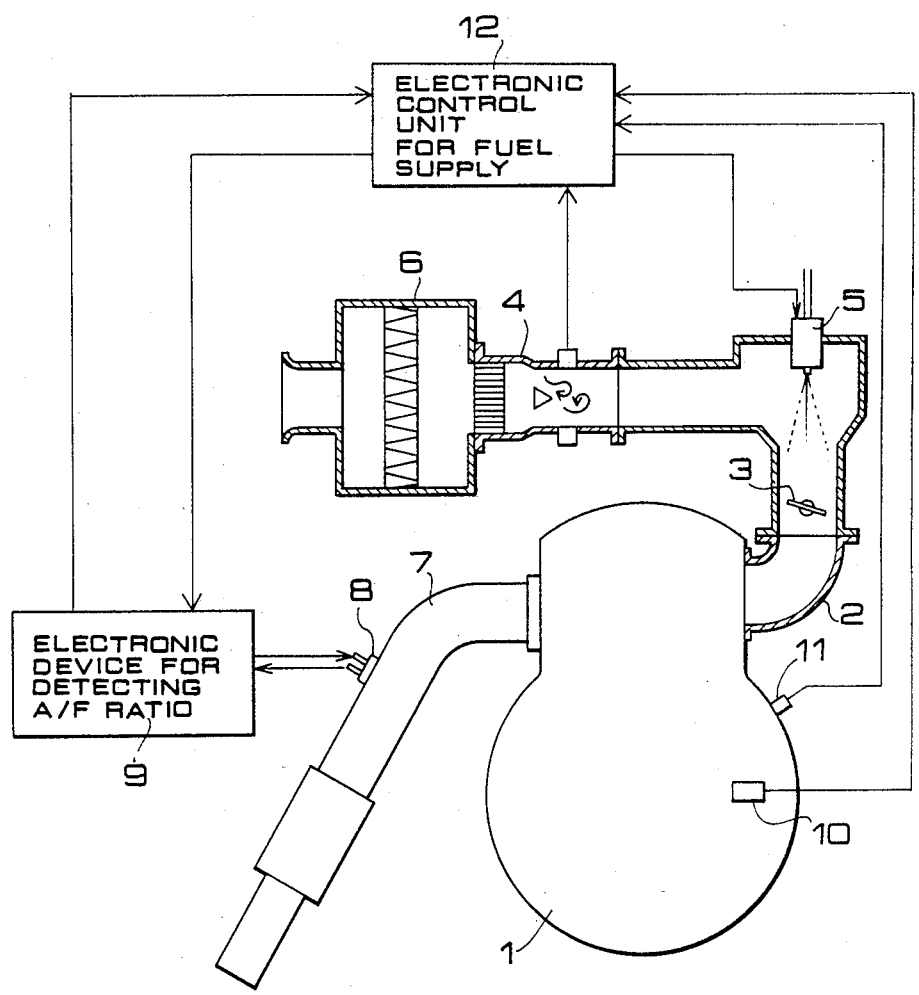
FIG. 1 shows an A/F ratio controller equipped with an A/F ratio sensor according to the present invention.

A preferred embodiment of the present invention will be described hereinafter in connection with the accompanying drawings. FIG. 1 shows a preferred embodiment of the present invention. In FIG. 1, indicated at 1 is an engine, at 2 a suction pipe of the engine 1, at 3 a throttle valve, at 4 a suction air quantity detecting unit for detecting the quantity of air sucked by the engine 1, at 5 a fuel feed valve disposed upstream with respect to the throttle valve 3, at 6 an air cleaner disposed upstream with respect to the suction air quantity detecting unit 4, at 7 the exhaust pipe of the engine 1, at 8 an A/F ratio sensor attached to the exhaust pipe 7, at 9 an electronic device for detecting A/F ratio, at 10 a revolving rate detector for detecting the revolving rate of the engine 1, at 11 a temperature detector for detecting the temperature of the engine 1 and at 12 an electronic control unit which receives the respective output signals of the temperature detector 11, the suction air quantity detecting unit 4, the electronic device 9 and the revolving rate detector 10 as input information and controls fuel feed rate by driving the fuel feed valve 5 according to the input information. As will be described in detail, the electronic control unit 12 has also a function to change over the direction of the pump current Ip of the A/F ratio sensor 8 according to the input information by driving the changeover switch SW of the electronic device for detecting A/F ratio.

Figure 3:
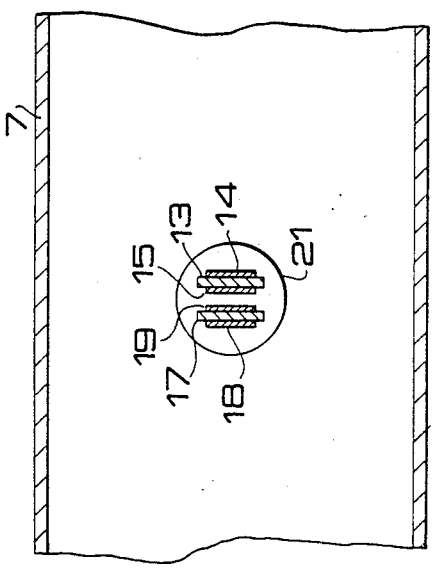
FIG. 3 is a sectional view taken along line II—II of FIG. 2.
Figure 2:
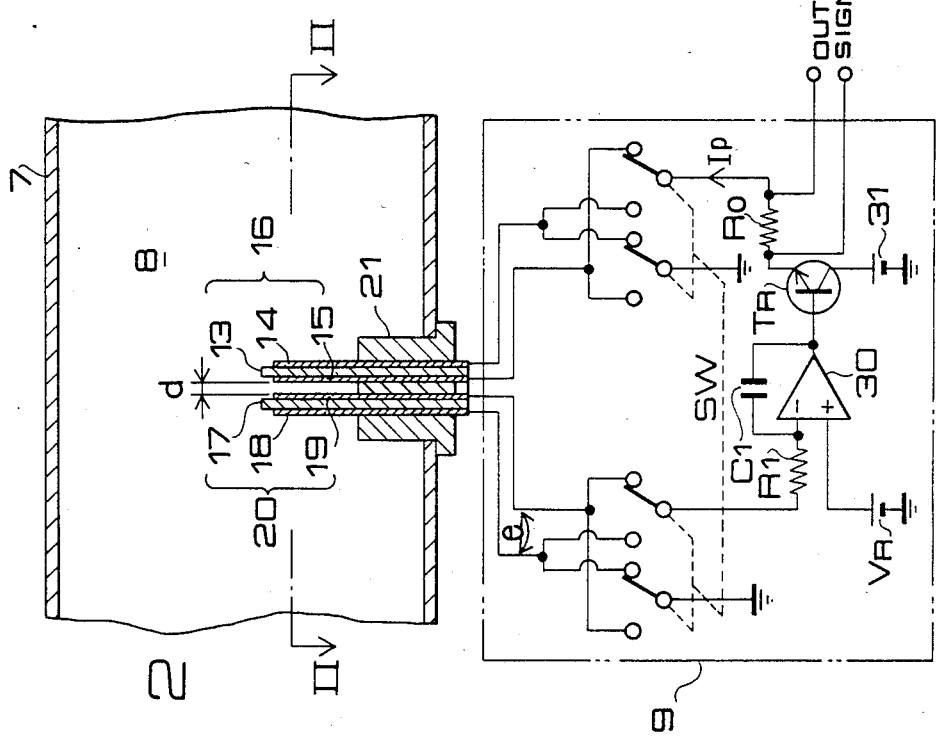
FIG. 2 is a combination of a longitudinal sectional view of the sensor unit of the A/F ratio controller of FIG. 1 and a circuit diagram of an electronic circuit for sensing A/F ratio.

FIG. 2 shows the detailed construction of the A/F ratio sensor 8 and the electronic device 9 and FIG. 3 is a sectional view taken along line II—II of FIG. 2. In this embodiment, the A/F ratio sensor 8 comprises a solid electrolyte oxygen pump 16 formed of a flat ion-conductive solid electrolyte plate 13, such as a flat plate of a stabilized zirconia 0.5 mm thick and provided on the opposite sides thereof with Pt electrodes 14 and 15, a solid electrolyte oxygen sensor 20 formed similarly to the oxygen pump 16 of the flat ion-conductive solid electrolyte plate 17 provided on the opposite sides thereof with Pt electrodes 18 and 19 respectively and a support 21 for supporting the oxygen pump 16 and the oxygen sensor 20 opposite to each other with a minute gap d having a width of about 0.1 mm therebetween.

The electronic device 9 for detecting A/F ratio includes an operational amplifier 30 having an inversion input terminal which receives an electromotive force e generated between the electrodes 18 and 19 of the oxygen sensor 20 through a resistance R1 and a non-inversion input terminal to which a reference voltage is applied by a reference voltage source $V_R$. A capacitor C1 is connected between the output terminal and the inversion input terminal of the operational amplifier 30. The output terminal of the operational amplifier 30 is connected to the base of a transistor TR and the collector of the transistor TR is connected to a DC power source 31. An output signal given through the emitter of the transistor TR is transmitted through a resistance $R_0$ as a pump current to the oxygen pump 16. The changeover switch SW consisting of mutually interlocked four switching elements is provided to change over the respective polarities of the electromotive force e which is supplied to the inversion input terminal of the operational amplifier 30 and the pump current Ip which is supplied to the oxygen pump 16.

The electromotive force e generated by the oxygen sensor 20 is compared with the voltage of the reference voltage source $V_R$ by the operational amplifier 30. The operational amplifier 30 gives a signal proportional to the difference between the electromotive force e and the voltage of the reference voltage source $V_R$ to the base of the transistor TR. Thus the pump current Ip that flows from the DC power source 31 through the transistor TR and the resistance $R_0$ to the oxygen pump 16 is controlled according to the electromotive force e generated by the oxygen sensor 20. A voltage generated at the opposite terminals of the resistance $R_0$ proportionally to the pump current Ip is taken out as an output signal.

Figure 4:
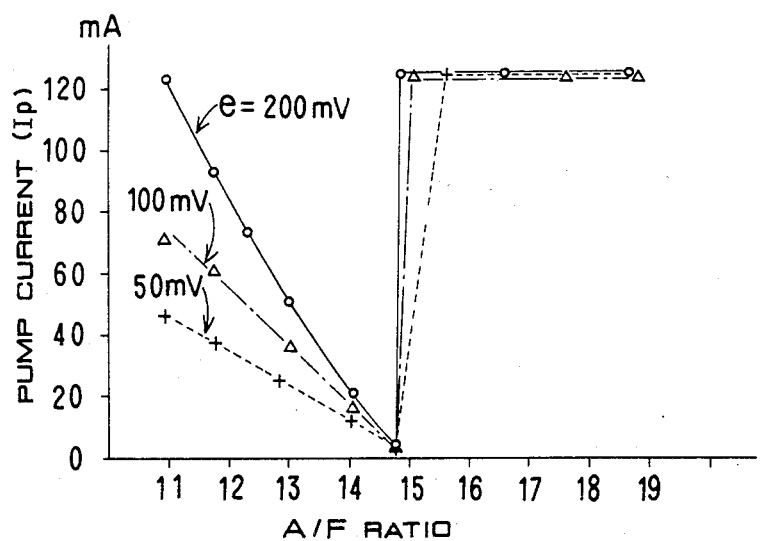
FIGS. 4 and 5 are graphs showing the characteristics of the A/F ratio sensor of FIG. 1 in the relation between A/F ratio and pump current for electromotive force as a parameter, in which the direction of the current supplied to the oxygen sensor in FIG. 4 is opposite to that in FIG. 5.
Figure 5:
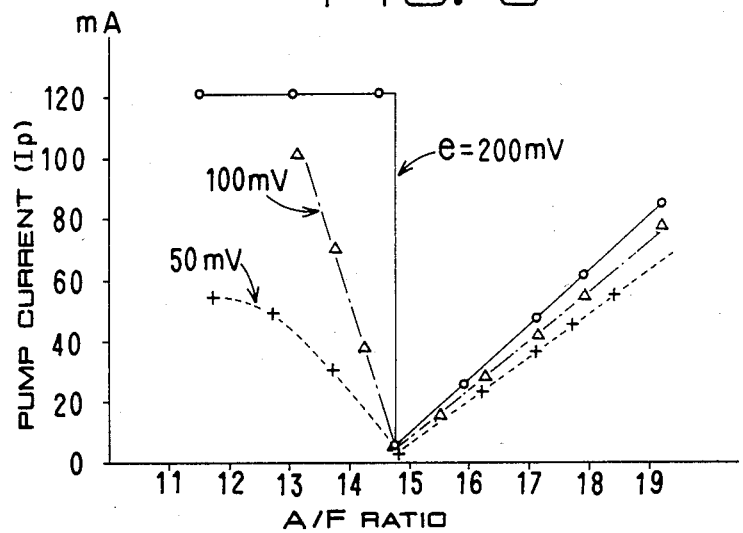

FIGS. 4 and 5 are graphs showing the characteristics of the A/F ratio sensor according to the present invention shown in FIG. 2, obtained through the test operation of a gasoline engine of 2000 cc nominal displacement equipped with the A/F ratio sensor 8 of the present invention for a domestic automobile. The upper limit of the pump current Ip was limited to 120 mA by the DC power source B, because an excessive pump current Ip damages the oxygen pump 16. The characteristics diagram of FIG. 4 shows the relation between the pump current Ip and the operating A/F ratio of the combustible mixture supplied to the engine for the variation of the electromotive force when the pump current Ip flows in the oxygen pump 16 from the electrode 15 disposed nearby the minute gap as a positive electrode to the electrode 14 as a negative electrode. In the test operation, the reference voltage was varied to control the electromotive force e at 200 mV, 100 mV and 50 mV so that the A/F ratio was changed accordingly. When the pump current Ip flows from the electrode 15 to the electrode 14, the oxygen partial pressure within the minute gap d becomes higher than the oxygen partial pressure outside the minute gap in the exhaust gas. Consequently, as generally known, an electromotive force e is generated in the oxygen sensor 20 with the electrode 19 disposed nearby the minute gap as a positive electrode. FIG. 5 shows the results of the test operation in which the changeover switch SW was arranged so that the pump current Ip would flow in the oxygen pump 16 from the electrode 14 to the electrode 15. In this case, on the contrary to the case of FIG. 4, the oxygen partial pressure within the minute gap becomes lower than the oxygen partial pressure outside the minute gap in the exhaust gas, and hence an electromotive force e is generated in the oxygen sensor 20 with the electrode 18 as a positive electrode. Accordingly, the changeover switch SW changes over the circuit so that the electrode 18 of positive polarity is connected to the inversion input terminal of the operational amplifier 30. In the results of the test shown in FIGS. 4 and 5, it is desirable that the rate of variation of the pump current Ip with the variation of A/F ratio is large in the vicinity of the stoichiometric A/F ratio (14.7) to attain the accurate detection of the stoichiometric A/F ratio. As apparent from FIGS. 4 and 5 showing the results of the test, according to the present invention, the electromotive force e is maintained at a fixed value above 100 mV, for example at 200 mV, where the rate of variation of the pump current around the stoichiometric A/F ratio is large, to attain the accurate detection of the stoichiometric A/F ratio. Furthermore, when it is desired to operate the engine in a region where the A/F ratio is smaller than the stoichiometric A/F ratio, namely, the fuel-rich region, the polarity of the pump current is selected so that the oxygen partial pressure within the minute gap d is greater than the oxygen partial pressure outside the minute gap in the exhaust gas, and hence the characteristics as shown in FIG. 4 is obtained, and thereby the variation of the pump current is proportional to A/F ratio in the fuel-rich region. On the contrary, if it is desired to operate the engine in a region where the A/F ratio is greater than the stoichiometric A/F ratio, namely, the fuel-lean region, the polarity of the pump current is selected so that the oxygen partial pressure within the minute gap d is smaller than the oxygen partial pressure outside the minute gap in the exhaust gas, and hence the characteristics as shown in FIG. 5 is obtained, and thereby the variation of the pump current is proportional to A/F ratio in the fuel-lean region. Thus an output signal corresponding to the pump current is obtained over a wide range of operating A/F ratio of the engine including the fuel-rich region and the fuel-lean region. The operating A/F ratio is controlled optionally through feedback control on the basis of the output signal.

As apparent from the characteristic curves shown in FIG. 4, when the electromotive force is 200 mV, the rate of variation of the pump current in the vicinity of the stoichiometric A/F ratio is large, and thereby the accurate detection of the stoichiometric A/F ratio is possible, however, it was found that the rate of variation of the pump current Ip is sufficiently large for practical purpose, when the electromotive force is 50 mV or greater.

The actions of the A/F ratio detector of the present invention will be described hereinafter. During the operation of the engine 1, the engine 1 sucks air from the atmosphere through the air cleaner 6, the suction air quantity detecting unit 4 and the suction pipe 2. The suction air quantity detecting unit 4 detects the suction air quantity. The electronic control unit 12 receives the output signal given by the suction air quantity detecting unit 4 and drives the fuel feed valve 5 so that an amount of fuel corresponding to the suction air quantity is injected into the engine 1. While the engine 1 remains cold as in a period immediately after starting, the electronic control unit 12 receives a low-temperature output signal of the temperature detector 11 and drives the changeover switch SW to change over the polarity of the pump current Ip of the A/F ratio sensor 8 so that the oxygen partial pressure within the minute gap d becomes higher than the oxygen partial pressure outside the minute gap d in the exhaust gas to operate the engine 1 at a desired operating A/F ratio, for example, A/F=12, within the rich A/F region. The desired operating A/F ratio is given from the characteristic curve of FIG. 4 as an output signal corresponding to the pump current. Upon the reception of the output signal corresponding to the pump current, the electronic control unit 12 controls the amount of fuel injected by the fuel feed valve so that the output signal coincides with a desired value. That is, the operating A/F ratio of the engine 1 is regulated at a desired value through feedback control on the basis of the output signal corresponding to the pump current. When the electronic control unit 12 detects the ordinary operating mode of the engine 1, such as an operating mode when the automobile is running in the urban area, on the basis of the output signals of the suction air quantity detecting unit 4 and the revolving rate detector 10, the electronic control unit 12 drives the changeover switch SW to change the polarity of the pump current Ip so that the oxygen partial pressure within the minute gap d becomes lower than the oxygen partial pressure outside the minute gap d in the exhaust gas to regulate the operating A/F ratio to a desired A/F ratio, for example, A/F=17, in the lean A/F region to operate the engine 1 at an economic fuel consumption ratio. The electronic control unit 12 detects the desired A/F ratio in the lean A/F region as an output signal corresponding to the pump current Ip from the characteristic curve of FIG. 5 and controls the fuel feed rate of the fuel feed valve 5 so that the output signal coincides with a desired vale. That is, the operating A/F ratio of the engine 1 is regulated through feedback control using the output signal.

When the electronic control unit 12 detects an engine operating mode in which the operating A/F ratio needs to be adjusted to the stoichiometric A/F ratio to reduce the contents of injurious components in the exhaust gas of the engine 1, from the output signals of the suction air quantity detecting unit 4, the revolving rate detector 10 and the temperature detector 11, the electronic control unit 12 adjusts the operating A/F ratio of the engine 1 to the stoichiometric A/F ratio in the same manner as that of the conventional controller through feedback control by using the Ip vs A/F ratio characteristics varying in steps in the vicinity of the stoichiometric A/F ratio as shown in FIG. 4 or in FIG. 5.

What is claimed is:

1. An air-to-fuel ratio detector for an engine, comprising:
    an air-to-fuel ratio sensor having an oxygen pump and an oxygen sensor disposed opposite to each other with a minute gap therebetween in an exhaust gas passage of said engine and each consisting of a flat plate of a solid electrolyte and electrodes attached to the opposite sides of the flat plate respectively;
    means for supplying a pump current to said oxygen pump;
    means for detecting the magnitude of an electromotive force of said oxygen sensor generated proportionally to the difference between the oxygen partial pressure within said minute gap and the oxygen partial pressure outside said minute gap by said oxygen pump supplied with a predetermined pump current;
    means for controlling the pump current to be supplied to said oxygen pump so that the electromotive force detected by said electromotive force detecting means is maintained at a fixed level;
    means for generating an air-to-fuel ratio detection output signal which is proportional to the pump current; and
    means for changing over the direction of the pump current supplied to said oxygen pump and the polarity of the output signal of said oxygen sensor simultaneously.

2. An air-to-fuel ratio detector according to claim 1, wherein said oxygen pump consists of a flat plate of an ion-conductive electrolyte having a thickness of about 0.5 mm and Pt electrodes provided on the opposite sides of the flat plate of the ion-conductive electrolyte respectively; said oxygen sensor consists of a flat plate of an ion-conductive electrolyte having a thickness of about 0.5 mm and Pt electrodes provided on the opposite sides of the flat plate of the ion-conductive electrolyte respectively, and a minute gap having a width of about 0.1 mm is formed between said oxygen pump and said oxygen sensor.

3. An air-to-fuel ratio detector according to claim 1 or 2, wherein said electromotive force detecting means is provided with an operational amplifier which compares the output of said oxygen sensor with a predetermined reference voltage and gives an output corresponding to the difference between the output of said oxygen sensor and the reference voltage.

4. An air-to-fuel ratio detector according to claim 3, wherein said pump current controlling means includes a transistor which controls the intensity of the pump current on the basis of the output of said operational amplifier.

5. An air-to-fuel ratio detector for an engine, comprising:
    an air-to-fuel ratio sensor having an oxygen pump and an oxygen sensor disposed opposite to each other with a minute gap therebetween in an exhaust gas passage of said engine and each consisting of a flat plate of a solid electrolyte and electrodes attached to the opposite sides of said flat plate respectively;
    means for supplying a pump current to said oxygen pump;
    means for detecting the magnitude of an electromotive force of said oxygen sensor generated proportionally to the difference between the oxygen partial pressure within said minute gap and the oxygen partial pressure outside said minute gap by said oxygen pump supplied with a predetermined pump current;
    means for controlling said pump current to be supplied to the oxygen pump so that the electromotive force detected by said electromotive force detecting means is maintained at a fixed level;
    means for changing over the direction of the pump current so that the oxygen partial pressure within said minute gap becomes lower than the oxygen partial pressure outside said minute gap when the operating air-to-fuel ratio of said engine needs to be controlled at an air-to-fuel ratio within a lean air-to-fuel region with respect to the stoichiometric air-to-fuel ratio and so that the oxygen partial pressure within said minute gap becomes higher than the oxygen partial pressure outside said minute gap when the operating air-to-fuel ratio of the engine needs to be controlled at an air-to-fuel ratio within a rich air-to-fuel region with respect to the stoichiometric air-to-fuel ratio, and for changing over the polarity of the output signal of said oxygen sensor;

means for generating an air-to-fuel ratio detection output which is proportional to the pump current; and means for controlling the fuel feed rate and/or the air feed rate on the basis of the air-to-fuel ratio detection output.

6. An air-to-fuel ratio detector according to claim 5, wherein a pump current which is sufficient to maintain the electromotive force generated by said oxygen sensor at a fixed value equal to or greater than 100 mV is supplied to said oxygen pump by said pump current supplying means.

* * * * *